(12) United States Patent
Paoletti

(10) Patent No.: US 7,534,442 B2
(45) Date of Patent: May 19, 2009

(54) IMMUNOGENIC COMPOSITIONS COMPRISING COVALENTLY BOUND POLYSACCHARIDES, ANTIGEN, AND BACTERIAL TOXOID

(75) Inventor: Lawrence C. Paoletti, Wilmington, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1364 days.

(21) Appl. No.: 10/223,675

(22) Filed: Aug. 20, 2002

(65) Prior Publication Data

US 2003/0170267 A1    Sep. 11, 2003

Related U.S. Application Data

(60) Provisional application No. 60/313,475, filed on Aug. 21, 2001.

(51) Int. Cl.
*A61K 39/21* (2006.01)
*A61K 39/00* (2006.01)
*A61K 39/385* (2006.01)
*A61K 39/09* (2006.01)

(52) U.S. Cl. ............ 424/208.1; 424/183.1; 424/197.11; 424/244.1

(58) Field of Classification Search .............. 424/188.1, 424/208.1, 193.1, 196.11, 197.11, 237.1, 424/244.1, 278.1, 183.1
See application file for complete search history.

(56) References Cited

U.S. PATENT DOCUMENTS

| | | | | |
|---|---|---|---|---|
| 4,284,537 | A | 8/1981 | Beachey | 260/6 |
| 4,413,057 | A | 11/1983 | Carlo et al. | 435/101 |
| 4,619,828 | A | 10/1986 | Gordon | 424/92 |
| 4,673,574 | A | 6/1987 | Anderson | 424/92 |
| 4,761,283 | A | 8/1988 | Anderson | 424/92 |
| 4,789,735 | A | 12/1988 | Frank et al. | 530/395 |
| 4,830,852 | A | 5/1989 | Marburg et al. | 424/85.8 |
| 4,902,502 | A | 2/1990 | Nitecki et al. | 424/83 |
| 5,302,386 | A | 4/1994 | Kasper et al. | 424/92 |
| 5,614,612 | A * | 3/1997 | Haigwood et al. | 530/395 |
| 5,651,971 | A | 7/1997 | Lees | 424/194.1 |
| 5,773,007 | A | 6/1998 | Penney et al. | 424/197.11 |
| 5,866,135 | A | 2/1999 | Blake et al. | 424/197.11 |
| 5,935,579 | A | 8/1999 | Habeshaw et al. | 424/188.1 |
| 5,965,714 | A | 10/1999 | Ryall | 530/402 |
| 5,968,521 | A | 10/1999 | Michel et al. | 424/197.11 |
| 5,993,825 | A | 11/1999 | Jennings et al. | 424/244.1 |
| 6,231,859 | B1 | 5/2001 | Kensil | 424/184.1 |
| 6,248,334 | B1 | 6/2001 | Lees et al. | 424/236.1 |

FOREIGN PATENT DOCUMENTS

| EP | 0 206 852 | 12/1986 |
|---|---|---|
| EP | 0 245 045 | 11/1987 |
| WO | WO 92/20370 | 11/1992 |

OTHER PUBLICATIONS

Johnston, M. I. 2000. The role of nonhuman primate models in AIDS vaccine development. Mol. Med. Today 6:267-270.*
Letvin, N. L. 1998. Progress in the development of an HIV-1 vaccine. Science 280:1875-1880.*
Haynes, B. F. 1996. HIV vaccines: where we are and where we are going. Lancet 348:933-937.*
Pantaleo, G., and R. A. Koup. 2004. Correlates of immune protection in HIV-1 infection: what we know, what we don't know, what we should know. Nat. Med. 10(8):806-810.*
Haigwood, N. L. 2004. Predictive value of primate models for AIDS. AIDS Rev. 6:187-198.*
Burton, D. R., and J. P. Moore. 1998. Why do we not have an HIV vaccine and how can we make one? Nature Med. Vac. Supl. (5):495-498.*
McMichael, A. J., and T. Hanke. 2003. HIV vaccines 1983-2003. Nat. Med. 9(7):874-880.*
Feinberg, M. B., and J. P. Moore. 2002. AIDS vaccine models: challenging challenge viruses. Nat. Med. 8(3):207-210.*
Desrosiers, R. C. 2004. Prospects for an AIDS vaccine. Nat. Med. 10(3):221-223.*
Shen, X., et al., 2001, Preparation and preclinical evaluation of experimental group B *streptococcus* type III polysaccharide-cholera toxin B subunit conjugate vaccine for intranasal immunization, Vaccine 19:850-861.*
Jann, K., and B. Jann, 1978, "Bacterial Polysaccharides", Meth. Enzymol. 50:251-272.*
Wessels, M. R., et al., 1998, "Structural Properties of Group B *Streptococcal* Type III Polysaccharide Conjugate Vaccines That Influence Immunogenicity and Efficacy", Infect. Immun. 66(5):2186-2192.*
Plante, O. J., et al., 2003, "Automated Synthesis of Polysaccharides", Meth. Enzymol. 369:235.*
Abstract of AH 1 above.
Bessler, et al., "Specific Antibodies Elicited by Antigen Covalently Linked to a Synthetic Adjuvant," *Immunobiol*. 170:239-245 (1985).
Ghose, et al., "Induction of Polyclonal and Monoclonal Antibody Responses to Cholera Toxin by the Synthetic Peptide Approach," *Molec. Immunol*. 25:223-230 (1988).
Jacob, et al., "Priming Immune Response to Chloera Toxin Induced by Synthetic Peptides," *Eur. J. Immunol*. 16:1057-1062 (1986).
Posnett, et al., "A Novel Method for Producing Anti-Peptide Antibodies," *J. Biol. Chem*. 263:1719-1725 (1988).
Shen, et al., "Preparation and Preclinical Evaluation of Experimental Group B *Streptococcus* Type III Polysaccharide-Cholera Toxin B Subunit Conjugate Vaccine for Intranasal Immunization," *Vaccine* 19:850-861 (2001).
Shen, et al., "Effect of Pre-Existing Immunity for Systemic and Mucosal Immune Responses to Intranasal Immunization with Group B *Streptococcus* Type III Capsular Polysaccharide-Cholera Toxin B Subunit Conjugate," *Vaccine* 19:3360-3368 (2001).

* cited by examiner

*Primary Examiner*—Jeffrey S. Parkin
(74) *Attorney, Agent, or Firm*—Michael A. Sanzo; Law Office of Michael A. Sanzo, LLC

(57) ABSTRACT

The present invention is directed to immunogenic conjugates comprised of a polymer, preferably a polysaccharide, with a covalently attached antigen and an agent for boosting a patient's immune response. The conjugates may be used in vaccines for a wide range of diseases.

20 Claims, No Drawings

IMMUNOGENIC COMPOSITIONS COMPRISING COVALENTLY BOUND POLYSACCHARIDES, ANTIGEN, AND BACTERIAL TOXOID

CROSS REFERENCE TO RELATED APPLICATION

The present application claims the benefit of U.S. provisional application Ser. No. 60/313,475, filed on Aug. 21, 2001.

STATEMENT OF GOVERNMENT FUNDING

The United States Government has a paid-up license in this invention and the right in limited circumstances to require the patent owner to license others in reasonable terms as provided for by the terms of NIH Grant No. 5R21AI4539102, awarded by the Department of Health and Human Services.

FIELD OF THE INVENTION

The present invention is directed to conjugate vaccines containing a polysaccharide or similar polymer, one or more covalently bound antigens and a covalently bound agent that induces a T cell dependent immune response. The invention also includes methods by which these vaccines are prepared and used.

BACKGROUND OF THE INVENTION

Vaccination represents one of medicine's most successful innovations. At the time that the polio vaccine was first introduced in the United States, more than 20,000 new cases of paralytic polio were reported annually. Today, the number of new cases approaches zero. Similar results have been obtained for measles, mumps, diphtheria, pertussis, and tetanus (Hinman, *Vaccines*, pp. 597, 595, S. Plotkin & E. Mortimer, Jr. ed., 1988). On a global level, vaccination has resulted in the eradication of smallpox (*World Health* 34:258 (1980)).

Despite these successes, there are many diseases that are not prevented by vaccination. Among the most important of these is AIDS. Although immunization probably offers the best hope of stemming the spread of this disease, particularly in developing countries, the development of an effective vaccine against AIDS has proven extraordinarily difficult. Among the many reasons that vaccines fail is that the antigens associated with a pathogen are only weakly immunogenic or that antigens mutate and assume new forms.

In general, vaccines have been prepared using whole, live, attenuated, heat or chemically killed bacteria or viruses, whole protein or peptide fragments, DNA, or purified polysaccharides. Polypeptides typically lead to T cell activation and prime a treated individual to secondary challenge, i.e., the individual responds more strongly if exposed to the same antigen at a later time. Unfortunately proteins and peptides often require the co-administration of adjuvants that may be toxic and stimulate the immune system in a non-specific way. Unlike proteins, polysaccharides are often capable of directly stimulating B cells to produce antibody without the need for T cell help. However, the response they generate tends to be relatively short and there is no priming to subsequent antigenic challenge.

In the last several years, attempts have been made to develop vaccines with improved properties by covalently coupling polypeptides and polysaccharides (see e.g. U.S. Pat. Nos. 5,773,007; 5,968,521; 5,866,135; 4,619,828). Initial successes with these vaccines led to improved methods for carrying out coupling reactions (U.S. Pat. Nos. 5,651,971; 6,248,334). As a result of these efforts, at least two conjugate vaccines are presently on the market; one for Haemophilus influenza type B infections (HibTITER®) and the other for pneumococcal diseases (Prevnar®). In both cases, the vaccines comprise an antigenic polysaccharide covalently bound to a diphtheria toxoid that enhances a patient's immune response. Additional improvements in the design of conjugates may lead to better vaccines and allow vaccination to be used for a wider range of diseases.

SUMMARY OF THE INVENTION

The present invention is based upon the discovery that a stronger immune response can be obtained from conjugate vaccines in which the conjugate is made up of three components, a polymer (preferably a polysaccharide), a covalently bound antigen and a covalently bound agent that boosts a subject's immune response. Conjugates of this type were found to give a substantially improved response to coat proteins derived from a Human Immunodeficiency Virus (HIV).

In its first aspect, the present invention is directed to an immunogenic composition in which there is a polymer covalently bound to a first antigen. The term "immunogenic" refers to a composition that induces a humoral immune response in an individual. Also bound to the polymer is an agent that boosts a subject's response to the first antigen. In general, this will be a bacterial toxoid, membrane protein or viral coat protein capable of inducing a strong T-cell response even in the absence of an adjuvant. Examples of specific proteins that may be used for this purpose are tetanus toxoid, diphtheria toxoid and hepatitis B core antigen.

Compositions will, preferably, use a polysaccharide with sialic acid groups for the polymer and group B streptococcal polysaccharides have been found to be particularly well suited for this purpose. Coupling may be carried out by any method known in the art. For example, antigen and booster molecules can be directly linked to sialic acid residues using an amination procedure or, alternatively, heterobifunctional or homobifunctional linkers may be used.

In another aspect, immunogenic compositions may be made which include, in addition to the first antigen and booster molecule, a second antigen also covalently bound to polymer. Preferably, the second antigen is endogenous to the same bacteria, virus, fungus or cell as the first antigen. The term "endogenous, as used in this context, refers to molecules native to the same organism. In this way, a single vaccine may be developed that presents multiple epitopes for the generation of antibodies to attack the same organism.

One of the main advantages of the compositions described above, is that the booster molecule serves the purpose of an adjuvant without the need for adding another non-specific or toxic immunostimulator to preparations. The ability of the booster-containing compositions to generate a greatly improved immune response was demonstrated using compositions containing the HIV env2-3 protein covalently bound to a group B streptococcal polysaccharide and with tetanus toxoid serving as the covalently bound booster. These preparations also contained the gp120 protein as a second antigen. Similar compositions should be effective with any of the antigens and polymers commonly administered to patients in vaccines.

In another aspect, the invention includes vaccines which contain the immunogenic compositions described above together with a pharmaceutically acceptable carrier. These vaccines may optionally also contain an adjuvant. The invention also encompasses methods of inducing an immune response in a subject by administering these vaccines at an effective dosage.

DETAILED DESCRIPTION OF THE INVENTION

Methods for forming immunogenic compositions from antigens and polymers have been described in scientific articles (see e.g., Jacob, et al., *Eur. J. Immunol.* 16:1057-1062 (1986); Bessler, *Immunobiol.* 170:239-244 (1985); Posnett, et al., *J. Biol. Chem.* 263:1719-1725 (1988); Ghose, et al., *Molec. Immunol.* 25:223-230 (1988)) as well as in patents and published patent applications (EP 245 045; U.S. Pat. Nos. 4,673,574; 4,761,283; 4,789,735; EP 206 852; U.S. Pat. Nos. 4,619,828; and 4,284,537). Any of the protein or peptide antigens that are presently used in vaccines may be covalently bound to polymer or polysaccharide to form a conjugate in accordance with the present invention. This is also true for the agents used to boost a patient's immune response. Particularly useful in this regard are the bacterial toxoids such as tetanus toxoid and diphtheria toxoid. Methods for obtaining these proteins are well known and they have been extensively used in conjugate vaccines. The term "toxoid" as used herein refers to a toxin which has been modified to retain its antigenicity without retaining its toxicity.

The size of polymers used in the invention will vary and, in the case of polysaccharides, will depend upon the bacteria from which they are derived. Polymers and polysaccharides can be as small as 1000 daltons or as large as $1 \times 10^6$ daltons but, in general, it is expected that they will have a molecular weight within the range of 5000 to 500,000 daltons. Particularly preferred polysaccharides are the type II and III group B streptococcus capsular polysaccharides. These may be obtained using methods described in U.S. Pat. Nos. 5,302,386 and 5,993,825.

The preferred method for coupling antigen and booster to polymer or polysaccharide is described in the Examples section below. This method is similar to that described in U.S. Pat. No. 4,902,502. Conjugates may be prepared by forming aldehyde groups on side chain terminal sugars of polysaccharides and then reacting these with the amine groups of polypeptides. Aldehydes may be formed by many methods, including selective hydrolysis or by oxidative cleavage, e.g., by periodate. Conjugation is preferably achieved by reductive amination in an aqueous solution containing cyanoborohydride anions. In a less preferred procedure, bifunctional coupling agents may be used as described in U.S. Pat. No. 4,830,852.

The immunogenic conjugates described above may be formulated into vaccines optionally containing salts, buffers, or other substances designed to improve the composition. Sterile solutions, e.g., phosphate buffered saline, may be used as the carrier and preservatives may be added to improve the stability of preparations during storage. Adjuvants should not normally be needed but may be used if desired. These would normally be mixed with compositions prior to administration but separate presentation to a subject may also be used. Adjuvants can take the form of oil based compositions, (e.g., Freund's complete and incomplete preparations), mineral salts (e.g., silica, kaolin, or carbon), polynucleotides or saponins. Examples of suitable materials for use in vaccines and methods for formulation are provided in Remington's Pharmaceutical Sciences (pp. 1324-1341, Mack Publishing Co., Easton, Pa. 1980)).

Vaccines or conjugates may be stored in a lyophilized form and reconstituted in a pharmaceutically acceptable carrier prior to administration. Alternatively, preparations may be stored in the vehicle itself. The volume of a single dose of the vaccine will vary but, in general, should be between about 0.1 ml and 1.5 ml and, more typically, between about 0.2 ml and 0.5 ml.

Any method for administering the vaccines to a patient which does not result in the destruction of immunogenic conjugates is compatible with the present invention. Generally, administration will be by parenteral means such as by intramuscular or intravenous injection. The dosage and scheduling of administration of vaccines can be determined using methods that are routine in the art. In general, it is expected that vaccines prepared by the methods disclosed herein will contain from 0.01-1,000 µg/ml per dose, preferably, between 0.1-500 µg/ml per dose, and, still more preferably between 10 and 300 µg/ml per dose. The preparations may be administered by either single or multiple injections.

EXAMPLES

I. Materials and Methods

Vaccines

Recombinant $gp120_{SF2}$ was expressed in CHO cells, and env2-3 ($HIV_{SF2}$) a full-length non-glycosylated gp120, was produced in yeast. Group B *Streptococcus* (GBS) type III capsular polysaccharide and monomeric tetanus toxoid (TT) were purified as described previously. GBS III CPS was treated with sodium periodate to create aldehydes on 73% of the total sialic acid residues as described. Gp120 was also treated with sodium periodate to create aldehydes on terminal sugar residues as follows: 0.958 mg of gp120 was suspended in 100 µl of 0.1 M sodium acetate buffer pH 5.6 containing 0.15 M NaCl. To this suspension was added 100 µl of 0.01 M freshly prepared sodium periodate, and the reaction was allowed to proceed for 10 minutes in the dark on ice. Ethylene glycol (50 µl) was then added to stop the reaction, and the oxidized protein was exhaustively dialyzed against PBST (40 mM sodium phosphate, 0.9% NaCl and 0.02% thimerosal). The elution profile of oxidized gp120 ($gp120_{ox}$) did not change after treatment with sodium periodate.

Five vaccines were prepared using the mixture of reactants shown in Table 1. Reactions were performed in Tube-O-Dialyzer™ (Geno Technology, Inc., St Louis, Mo.) microtubes. The reductive amination reaction was initiated by the addition to each mixture of 7 to 10 mg of sodium cyanoborohydride (Matreya, Inc, Pleasant Gap, Pa.) and proceeded for 14 days at 37° C. with vortexing. Aliquots were taken before the addition of sodium cyanoborohydride and stored at −20° C. Additional sodium cyanoborohydride (7 to 15 mg) was added on days 7, 12, and 13. Day 0 and 14 aliquots, diluted 1:1 with PBST, were separated with a Sepharose 6 PC gel filtration column (3.2 mm×300 mm, Amersham Pharmacia Biotech, Inc., Piscataway, N.J.) and a ProStar HPLC system (Varian, Inc., Walnut Creek, Calif.) equipped with a UV/VIS detector with a microbore flow cell. The caps of the microtubes were replaced with ones containing a dialysis membrane with a 8,000 molecular weight cut off, and the tubes were inverted membrane-side down in a float and contents exhaustively dialyzed against PBST for 4 days at room temperature. No further manipulations were made to the dialyzed vaccine constructs. Vaccines were stored at 4° C.

Immunogenicity Studies

Groups of five Balb/c mice each received three intraperitoneal injections of the individual conjugate preparations on day 0, 28, and 52. Each 0.5 ml dose delivered 5 μg as protein and 10 μg of the adjuvant quil A. Control groups of mice are similarly immunized with uncoupled gp120, uncoupled env2-3, or as GBS type III CPS conjugated to TT (III-TT). Serum was obtained before vaccination and on days 28, 50, 73 and 114. A group of CD-1 outbred mice (n=4 or 5 per group) received gp120-TT-III conjugate or the unconjugated control gp120+TT+III mixed 1:1 with AlOOH adjuvant (Al-hydrogel 1.3%, Superfos Biosector, Vedbaek, Denmark). Mice received booster doses of these vaccines with adjuvant by the same route three weeks after the primary dose. Antibody responses to TT and GBS type III CPS in serum from these mice are measured by ELISA according to previously described methods.

Gp120 ELISA

HIV gp120-specific IgG titers were determined by direct ELISA. Briefly, HIV gp120$_{SF2}$ (100 ng/well in 50 μl) was adsorbed to microtiter plates and nonspecific sites were blocked with 10% goat serum for 1 hour at 37° C. Wells are washed three times with PBS containing Tween 20 and mouse serum diluted in goat serum is added to the antigen coated wells and incubated for 1 hour at 37° C. Wells were washed to remove unbound antibody, then a goat anti-mouse IgG conjugated to horseradish peroxidase and used at a 1:00,000 dilution was added to the wells, and incubated for 1 hour at 37° C. After washing with PBS containing Tween 20 the substrate ABTS was added along with $H_2O_2$. The enzyme reaction is stopped by adding sodium dodecyl sulfate, and the binding of the antibody to the antigen is quantified spectrophotometrically.

Peripheral Blood Mononuclear Cells

Peripheral blood mononuclear cells (PBMC) were isolated from donor blood (Silvan Goldman Blood Institute, Oklahoma City, Okla.) on Ficoll hypaque gradients using standard procedures. Plasma from each donor sample was pre-screened by ELISA for HIV-1 p24 and antibodies to HIV-1 gp120. The PBMCs were blasted for three days in RPMI medium supplemented with 10% Fetal Bovine Serum (FBS), recombinant human IL-2 (10 μg/ml) and phytohemaglutinin (PHA) (5 μg/ml) prior to infection.

Virus Stocks

HIV-1 primary isolates were obtained from the AIDS Research and Reference Reagent Program, Rockville, Md. Stocks were expanded in fresh human PBMC blasts by weekly co-culture. Briefly, $2\times10^6$ blasts were washed in saline and pelleted by centrifugation for ten minutes at 400×g. Cell pellets were infected with 200 μl, of viral stock for one hour at 37° C. shaking every 15 minutes. After one hour the virus inoculum was washed away with saline and the infected cells were resuspended in two ml of RPMI/IL-2 medium and plated in individual wells of a 24-well tissue culture plate. On day four, one ml of culture was removed and replaced with one ml of fresh medium. On day seven, one ml of culture was removed and replaced with one ml of $2\times10^6$ fresh blasts. The HIV-1 isolates used in neutralization assays are listed in a table below. The stock titers ranged from $1\times10^2$ to $1\times10^4$ tissue culture infectious doses $(TCID)_{50}$/ml. Laboratory isolates of HIV-1 were grown identically except for the use of the cloned human T-cell line Sup T1.

Antigen Capture ELISA

Briefly, individual wells of 96-well microtiter plates were coated with (50 μl) anti-p24 Mab (10 μg/ml) diluted in borate buffered saline (BBS) for one hour at 37° C. The coating solution was removed and unbound sites were blocked by addition of (200 μl) 5% goat serum diluted in BBS for 30 minutes at 37° C. The blocking solution was removed and the wells washed five times with BBS containing 0.05% Tween-20 (BBST). Samples and controls (50 μl) were added to the wells and incubated for one hour at 37° C. The samples were removed and the wells were washed five times with BBST. HIV Immunoglobulin (HIV-Ig) was obtained from the AIDS Research and Reference Reagent Program and labeled with Horseradish Peroxidase (HRP). A pretitrated dilution (1:100) of the HIV-IgHRP (50 μl) was added to the wells for one hour at 37° C. The HIV-Ig-HRP was removed and the wells were washed five times with BBST. The assay was developed by addition of (50 μl) tetramethylbenzidine (TMB). The development was stopped after 30 minutes by addition of (20 μl) one molar HCl and read at an OD of 450 nm in a microplate reader.

$TCID_{50}$ Determination

HIV-1 stocks were serially diluted one to ten in saline and $2\times10^6$ PBMC blasts were infected for one hour at 37° C. The virus inoculum was washed away with saline and the cells were resuspended in one ml of medium. The cells were then aliquoted into ten wells of a 96-well tissue culture plate (100 μl/well). On day four, 100 μl of fresh medium was added and on day seven the wells were tested for the presence of HIV-1 p24. The $TCID_{50}$/ml was determined using the Reed-Muench method. Laboratory isolates of HIV-1 were assayed identically only utilizing the cloned T-cell line Sup T1.

Neutralization Assay

Fresh three day blasted human PBMC or Sup T1 cells $2\times10^6$ per experiment, were harvested and washed two times in saline. The virus inoculums, 50 $TCID_{50}$ in 200 μl, were pre-treated for one hour with a 1:20 dilution of immune sera. The positive control for the neutralization experiments was the anti-CD4 Mag designated P1, a murine IgG1k. Positive control cells samples were pre-treated with P1 (100 μg/ml) for one hour at 37° C. The infections were shaken every 15 minutes during the adsorption period after which the PBMC were pelleted for 10 minutes at 400×g and unadsorbed virus was washed away with saline. Finally, the infections were resuspended in two ml RPMI/IL-2 medium and added to individual wells of 24-well tissue culture plates. Infections were fed on days four and seven by removing one ml of culture and replacing with it one ml fresh medium. The level of infectivity was determined based on OD values from the HIV-1 p24 antigen capture ELISA.

Statistical Analysis

An unpaired means comparison, 2-tailed T test was performed on log transformed IgG titers using Statview version 5.0 (SAS Institute Inc., Cary, N.C.).

II. Results

Conjugate Vaccines

Optimization studies were performed for most of the constructs to determine the conditions necessary to generate conjugate vaccines for testing in mice. For example, when sodium cyanoborohydride (1.5 mg) was added to a mixture of gp120 (34 μg) and TT (46 μg) and oxidized type III CPS (82 μg), a progressive shift to the left of the monomer peak (representing both TT and gp120, 15.8 min.) towards the void volume of the column (8.9 min.) resulted. A broad intermediate size polymer (11.7 min) with a concomitant decrease in the monomer peak formed over 4 days. This shift to large molecular weight polymers (exclusion limit for globular proteins on the Superose 6 PC column is $4\times10^7$) is a hallmark of covalent coupling between the reactants.

The elution profiles were examined for reactants before and 14 days after the reductive amination coupling reaction was initiated for the vaccine. Before initiation of the conjugation reaction, the predominant protein peak eluting between 15.8 and 16.1 min., corresponding to both TT monomer (150 kDa) and gp120 (120 kDa), was visualized. Two weeks after the conjugation reaction was initiated, polymers of higher molecular mass were formed as determined by shifts to the left of the protein profiles. Gp120 in combination with TT and oxidized type III CPS formed polymers of high molecular mass (peak at 12.4 min.) in the presence of sodium cyanoborohydride whereas little to no coupling or loss of the monomer peak was evident in the absence of the reductant. Similar protein shifts with peak maxima at 13.6 min and 00.0 min were observed after 2 weeks for the env2-3-TT-III, and env-2-3-gp120-TT-III constructs, respectively. Other than a decrease in the amount of monomer peak, and, the elution profile of the gp120ox-TT construct showed little change after two weeks of conjugation.

Exhaustive dialysis of the constructs was performed to remove sodium cyanoborohydride and to exchange the buffer to PBST. Post-dialysis indication of the removal of this chemical was determined by gel filtration chromatography and detection at 280 nm. The large sodium cyanoborohydride peak at 15.8 min. from the gp120-TT-III conjugation was absent after dialysis.

Immunogenicity Studies

A pilot experiment in outbred mice confirmed that all three components (gp120, TT and type III CPS) in one conjugate (gp120-TT-III) were immunogenic. Three separate ELISAs measured, respectively, increases in IgG specific for GBS type III CPS, TT, and gp120 following two doses of 2.5 µg as gp120/env2-3 per dose with alum. In comparison, gp120+TT+III vaccine elicited low to moderate increases in IgG specific for gp120 and type III CPS, and a high increase in TT-specific IgG.

Four conjugated and four unconjugated control vaccines combined with Quil A adjuvant were administered to inbred Balb/c mice. The geometric mean titer (GMT) of gp120-specific IgG in sera from all groups before vaccination was <50. After receiving the primary and a booster dose of env2-3-TT-III conjugate vaccine the gp120-specific IgG GMT rose to 249, then peaked at 3,031 three weeks after mice received the third dose. Similarly, the GMT in sera from mice after two and three doses of env2-3-gp120-TT-III conjugate vaccine was 1,315, and 4,756, respectively. The peak gp120-specific IgG GMT in mice that received three doses of the gp120$_{ox}$-TT or gp120-TT-III conjugate vaccine was 668 and 173, respectively. In contrast, three control vaccines (gp120, gp120-TT-III, and III-TT) elicited GMTs <80. Uncoupled env2-3 vaccine elicited a gp120-specific IgG GMT of 562 three weeks after the third dose which rose slightly at day 114.

Neutralizing Activity

Pooled mouse sera, obtained on day 73 and diluted 1:20, was used to inhibit HIV-1$_{MN}$ infection of SupT1 cells. Sera from mice that received three doses of env-gp120–TT-III conjugate vaccine neutralized 100% and 85% of HIV-1$_{MN}$ at 5 and 50 TCID$_{50}$/ml, respectively. In the same system, sera from mice that received env-TT-III neutralized 55% of 5 TCID$_{50}$/ml inoculum, which declined to 5% when the dose was 50 TCID$_{50}$/ml. No sera, prevaccination sera, and sera from mice that received the other conjugate vaccines (gp120-TT-III, gp120ox-TT, TT-III), mixtures (gp120+TT+III), or uncoupled proteins (gp120, env) neutralized $\leq$12% of 5 TCID$_{50}$/ml inoculum. P1 serum (100 µg/ml) neutralized $\geq$95% of HIV-1$_{MN}$ tested at 5-5,000 TCID$_{50}$/ml inocula.

Pooled sera from env-gp120-TT-III-vaccinated mice inhibited 50% and 12% infection of human PBMC by HIV-1$_{MN}$ or HIV-1$_{BRO14}$ whereas sera from mice that received the other vaccines, or uncoupled gp120 or env2-3 resulted in less than 10% inhibition.

TABLE 1

Conjugation reactions

| Construct | Amount (µg) of each reactant in the reaction mixture: | | | | Volume (µl) | Comment |
| --- | --- | --- | --- | --- | --- | --- |
| | gp120 | TT | III$_{ox}$CPS$^a$ | Env2-3 | | |
| gp120–TT–III | 300 | 217 | 621 | 0 | 175$^b$ | Test |
| gp120+TT+III | 300 | 214 | 626 | 0 | 175$^b$ | Control (no NaCNBH$_4$) |
| env2-3–TT–III | 0 | 200 | 779 | 300 | 250$^c$ | Test |
| env2-3-gp120–TT–III | 150 | 204 | 600 | 150 | 213$^d$ | Test |
| gp120–TT | 200$^e$ | 113 | 0 | 0 | 143' | Test |

$^a$Periodate oxidized group B streptococcal type III capsular polysaccharide,
$^b$40 mM sodium citrate, 280 mM NaCl, pH 6.0,
$^c$PBS, pH 7.4 containing 0.190 SDS and 2 mM EDTA,
$^d$A 1:1 ratio of buffers used in footnotes b and c,
$^e$Periodate-oxidized gp120,
$^f$40 mM sodium phosphate, 320 mM NaCl, 0.02% thimerosal.

TABLE 2

Immune response in CD-1 outbred mice to vaccination with gp120 coupled to GBS type III CPS and TT (gp120–TT III) or as an uncoupled mixture (gp120+TT+III) with alum adjuvant.

| Vaccine | Antibody Specificity | GMC (range) of antisera obtained on day: | |
| --- | --- | --- | --- |
| | | 0 | 63 |
| gp120–TT–III | gp120 | 100 (100) | 476 (200-800) |
| | TT | 100 (100) | 54,000 (16,000-256,000) |
| | III CPS | 100 (100) | 27,000 (16,000-64,000) |

TABLE 2-continued

Immune response in CD-1 outbred mice to vaccination with gp120 coupled to GBS type III CPS and TT (gp120–TT III) or as an uncoupled mixture (gp120+TT+III) with alum adjuvant.

| Vaccine | Antibody Specificity | GMC (range) of antisera obtained on day: | |
|---|---|---|---|
| | | 0 | 63 |
| gp120+TT+III | gp120 | 100 (100) | 200* (100-400) |
| | TT | 100 (100) | 215,000 (128,000-256,000) |
| | IIICPS | 100 (100) | 2,400 (2,000-4,000) |

Four mice per group were intraperitoneally administered two doses (day 0 and day 21) of 2.5 μg vaccine as gp120/env2-3 per dose with alum as the adjuvant.
*Two of 4 mice responded.

TABLE 3

Immunogenicity in Balb/c mice (n = 5/group) of HIV gp120-containing vaccine constructs.

| Vaccine Construct | Geometric mean titer (range) [95% confidence interval] of HIV gp 120$_{SF2}$-specific IgG in sera obtained on day: | | | | |
|---|---|---|---|---|---|
| | 0 | 28 | 50 | 73 | 114 |
| 1. env2-3-TT–III | 50 (50) [—] | 50 (50) [—] | 249 (50-16,000) [14-1,520] | 3,031$^\pm$ (500-32,000) [381-24,099] | 1,000 (500-2,000) [423-2,366] |
| 2. env2-3-gp120–TT–III | 50 (50) [—] | 50 (50) [—] | 1,315 (150-12,800) [181-9,572] | 4,756$^{a\#}$ (4,000-8,000) [2,741, 8,260] | 1,189$^a$ (500-2,000) [414-3,420] |
| 3. gp120$_{ox}$TT | 50 (50) [—] | 50 (50) [—] | 372$^a$ (50-1,600) [23-5,956] | 668$^a$ (50-8,000) [19-23,605] | 266$^a$ (50-2,000) [12-5,929] |
| 4. gp120–TT–III | 50 (50) [—] | 50 (50) [—] | 51 (50-60) [—] | 173 (50-500) [40-740] | 126 (50-500) [26-601] |
| 5. env2-3 | 50 (50) [—] | 50 (50) [—] | 68 (50- 200) [32-145] | 562$^a$ (50-8,000) [18-17,258] | 794$^b$ (50-2,000) [109-5,794] |
| 6. gp120 | 50 (50) [—] | 50 (50) [—] | 57 (50-100) [39-84] | 68 (50-250) [28-168] | 79 (50-500) [22-284] |
| 7. gp120+TT+III | 50 (50) [—] | 50 (50) [—] | 50 (50) [—] | 50 (50) [-] | 50 (50) [-] |
| 8. III–TT | 50 (50) [—] | 50 (50) [—] | 50 (50) [—] | 50 (50) [-] | 50 (50) [-] |

Vaccines were administered at day 0, 28, and 52.
$^a$n = 4 mice.
$^b$n =3 mice.
$^\pm$P < 0.05 compared to vaccines 4, 6-8; and P > 0.10 compared to vaccines 2, 3 and 5.
$^\#$P < 0.05 compared to vaccines 4, 6- 8 P < 0.10 compared to vaccine 5; and P > 0.10 compared to vaccines 1 and 3.

TABLE 4

Inhibition of HIV-1$_{MN}$ infection of SupT1 cells by vaccine sera.

| | HIV-1$_{MN}$ Inoculum TCID$_{50}$/ml) | | | |
|---|---|---|---|---|
| Sera | 5 | 50 | 500 | 5,000 |
| None | 0.0 | 0.0 | 0.0 | 0.0 |
| Pre-sera | 0.0 | 0.0 | 0.0 | 0.0 |
| P1 | 99.0 | 95.0 | 97.0 | 96.0 |
| gp120-TT-III | 0.0 | 0.0 | 0.0 | 0.0 |
| env-TT-III | 55.0 | 5.0 | 0.0 | 0.0 |
| env-gp120-TT-III | 100.0 | 85.0 | 14.0 | 0.0 |
| gp120$_{ox}$-YF | 12.0 | 0.0 | 0.0 | 0.0 |
| gp120+TT+III | 0.0 | 0.0 | 0.0 | 0.0 |
| gp120 | 0.0 | 0.0 | 0.0 | 0.0 |
| env2-3 | 10.0 | 0.0 | 0.0 | 0.0 |
| TT-III | 0.0 | 0.0 | 0.0 | 0.0 |

A 1:20 dilution of pooled sera obtained on day 73 from mice immunized three times with each particular vaccine was used as inhibitor. At day seven post-infection samples were taken and assayed in triplicate for HIV-1 p24 by antigen capture ELISA. Values represent the percent inhibition compared to control infections. The positive inhibitor was the anti-CD4 monoclonal antibody designated P1 (100 µg/ml).

TABLE 5

Inhibition of HIV-1$_{MN}$ or HIV-1$_{BRO14}$ infection of Sup T1 cells or human PBMC blasts by vaccine sera.

| | HIV-1$_{MN}$ | | HIV-1$_{BRO14}$ | |
|---|---|---|---|---|
| Vaccine Sera | Sup T1 | PBMC | Sup T1 | PBMC |
| None | 0.0 | 0.0 | 0.0 | 0.0 |
| Pre-sera | 0 | 0.0 | 0.0 | 0.0 |
| P1 | 100.0 | 90.0 | 100.0 | 95.0 |
| gp120-TT-III | 0.0 | 0.0 | 0.0 | 0.0 |
| env-TT-III | 45.0 | 8.0 | 22.0 | 0.0 |
| env-gp120-TT-III | 95.0 | 50.0 | 75.0 | 12.0 |
| gp120$_{ox}$-TT | 10.0 | 0.0 | 0.0 | 0.0 |
| gp120+TT+III | 0.0 | 0.0 | 0.0 | 0.0 |
| Sp120 | 0.0 | 0.0 | 0.0 | 0.0 |
| env2-3 | 5.0 | 0.0 | 0.0 | 0.0 |
| TT-III | 0.0 | 0.0 | 0.0 | 0.0 |

Three day human PBMC blasts or Sup TI cells were infected with 50 TCID$_{50}$/ml of either HIV-1$_{MN}$ or HIV-1$_{BRO14}$. A 1:20 dilution of pooled sera obtained on day 73 from mice immunized three times with each particular vaccine was used as inhibitor. At day seven post-infection, samples were taken and assayed in triplicate for HIV-1 p24 by antigen capture ELISA. Values represent the percent inhibition compared to control infections. The positive inhibitor was the anti-CD4 murine monoclonal antibody designated P1 (100 µg/ml).

TABLE 6

Human immunodeficiency virus type one primary isolates

| Virus | Origin | Subtype (gag/env) | Coreceptor Usage (biotype) | Titer (TCID$_{50}$/mL) |
|---|---|---|---|---|
| 92UG029 | Uganda | A/A | X4 (SI) | 1,000 |
| 92BRO14 | Brazil | B/B | R5X4 (SI) | 1,000 |
| 931N905 | India | C/C | R5 (SI) | 1,000 |
| 92UG001 | Uganda | D/D | R5X4 (SI) | 10,000 |
| 92TH005 | Thailand | A/EA | R5 (NSI) | 1,000 |

HIV-1 primary isolates were obtained from the AIDS Research and Reference reagent program. Subtyping was determined by sequencing a short sequence of the gag and/or env genes, or by HMA; thus, intersubtype recombinants may not have been detected in some cases. Biotypes determined by MT-2 syncytium assay. Syncytium-inducing (SI) and non-syncytium-inducing (NSI) variants may exist in the viral swarm for each isolate.

TABLE 7

Inhibition of HIV-1 subtype A, B, C, D, and E infection of human PBMC blasts by vaccine sera.

| | HIV-1 Subtype | | | | |
|---|---|---|---|---|---|
| Vaccine Sera | A | B | C | D | E |
| None | 0.0 | 0.0 | 0.0 | 0.0 | 0.0 |
| Pre-sera | 0.0 | 0.0 | 0.0 | 0.0 | 0.0 |
| P1 | 95.0 | 98.0 | 96.0 | 99.0 | 98.0 |
| gp120-TT-III | 0.0 | 0.0 | 0.0 | 0.0 | 0.0 |
| env-TT-III | 0.0 | 12.0 | 0.0 | 0.0 | 0.0 |
| env-gp120-TT-III | 0.0 | 64.0 | 0.0 | 0.0 | 0.0 |
| gp120$_{ox}$-TT | 0.0 | 0.0 | 0.0 | 0.0 | 0.0 |
| gp120+TT+III | 0.0 | 0.0 | 0.0 | 0.0 | 0.0 |
| gp120 | 0.0 | 0.0 | 0.0 | 0.0 | 0.0 |
| env2-3 | 0.0 | 0.0 | 0.0 | 0.0 | 0.0 |
| TT-III | 0.0 | 0.0 | 0.0 | 0.0 | 0.0 |

A 1:20 dilution of pooled sera obtained on day 73 from mice immunized three times with each particular vaccine was used as inhibitor. At day seven post-infection, samples were taken and assayed in triplicate for HIV-1 p24 by antigen capture ELISA. Values represent the percent inhibition compared to control infections. The positive inhibitor was the murine anti-CD4 specific monoclonal antibody designated P1 (100 µg/ml).

All references cited are fully incorporated by reference. Having now fully described the invention, it will be understood by those of skill in the art that the invention may be performed within a wide and equivalent range of conditions, parameters, and the like, without affecting the spirit or scope of the invention or any embodiment thereof.

What is claimed is:

1. An immunogenic composition comprising
    a) a group B streptococcal polysaccharide of $1\times10^3$-$1\times10^6$ daltons;
    b) HIV-1 env2-3 bound directly to said polysaccharide by a covalent bond; and
    c) a booster that is either tetanus or diptheria toxoid bound directly to said polysaccharide by a covalent bond.

2. The immunogenic composition of claim 1, further comprising HIV-1 gp120 covalently bound to said polysaccharide.

3. The immunogenic composition of claim 1, wherein said HIV-1 env2-3 and said tetanus or diptheria toxoid are covalently bound to sialic acid groups on said group B streptococcal polysaccharide.

4. The immunogenic composition of claim 3, further comprising HIV-1 gp120 covalently bound to sialic acid groups on said group B streptococcal polysaccharide.

5. The immunogenic composition of claim 4, wherein said HIV-1 env2-3, said booster and said HIV-1 gp120 are joined to said sialic acid groups using an amination procedure.

6. The immunogenic composition of claim 4, wherein said HIV-1 env2-3, said booster and said HIV-1 gp120 are joined to said sialic acid groups by a heterobifunctional or homobifunctional linker.

7. The immunogenic composition of claim 1, wherein said booster is tetanus toxoid.

8. The immunogenic composition of claim 1, wherein said polysaccharide has a molecular weight of 5000 to 500,000 daltons.

9. The immunogenic composition of claim 7, further comprising HIV-1 gp120 covalently bound to said polysaccharide.

10. The immunogenic composition of claim 9, wherein said polysaccharide has a molecular weight of 5000 to 500,000 daltons.

11. The immunogenic composition of claim 9, wherein said HIV-1 env2-3 and said tetanus toxoid are covalently bound to sialic acid groups on said group B streptococcal polysaccharide.

12. The immunogenic composition of claim 11, further comprising HIV-1 gp120 covalently bound to sialic acid groups on said group B streptococcal polysaccharide.

13. The immunogenic composition of claim 12, wherein said HIV-1 env2-3, said booster and said HIV-1 gp120 are joined to said sialic acid groups using an amination procedure.

14. The immunogenic composition of claim 12, wherein said HIV-1 env2-3, said booster and said HIV-1 gp120 are joined to said sialic acid groups by a heterobifunctional or homobifunctional linker.

15. An immunogenic composition consisting of:
a) a group B streptococcal polysaccharide of $1\times10^3$-$1\times10^6$ daltons;
b) HIV-1 env2-3 bound directly to said polysaccharide by a covalent bond;
c) a booster that is either tetanus or diptheria toxoid bound directly to said polysaccharide by a covalent bond.
d) HIV-1 gp120 bound directly to said polysaccharide by a covalent bond.

16. The immunogenic composition of claim 15, wherein said HIV-1 env2-3, said booster and said HIV-1 gp120 are covalently bound to sialic acid groups on said group B streptococcal polysaccharide.

17. The immunogenic composition of claim 16, wherein said HIV-1 env2-3, said booster and said HIV-1 gp120 are joined to said sialic acid groups using an amination procedure.

18. The immunogenic composition of claim 16, wherein said HIV-1 env2-3,said booster and said HIV-1 gp120 are joined to said sialic acid groups by a heterobifunctional or homobifunctional linker.

19. The immunogenic composition of claim 16, wherein said booster is tetanus toxoid.

20. The immunogenic composition of claim 19, wherein said polysaccharide has a molecular weight of 5000 to 500,000 daltons.

* * * * *